(12) United States Patent
Bai et al.

(10) Patent No.: US 9,328,053 B2
(45) Date of Patent: *May 3, 2016

(54) METHYL-SUBSTITUTED BIPHENYL COMPOUNDS, THEIR PRODUCTION AND THEIR USE IN THE MANUFACTURE OF PLASTICIZERS

(71) Applicant: ExxonMobil Chemical Patents Inc., Baytown, TX (US)

(72) Inventors: Chuansheng Bai, Phillipsburg, NJ (US); Jihad M. Dakka, Whitehouse Station, NJ (US); Lorenzo C. DeCaul, Langhorne, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/201,226

(22) Filed: Mar. 7, 2014

(65) Prior Publication Data

US 2014/0275606 A1 Sep. 18, 2014

Related U.S. Application Data

(60) Provisional application No. 61/781,116, filed on Mar. 14, 2013.

(51) Int. Cl.
- *C07C 67/08* (2006.01)
- *C07C 5/367* (2006.01)
- *C07C 2/76* (2006.01)

(52) U.S. Cl.
CPC . *C07C 67/08* (2013.01); *C07C 2/76* (2013.01); *C07C 5/367* (2013.01); *C07C 2101/14* (2013.01); *C07C 2521/04* (2013.01); *C07C 2521/08* (2013.01); *C07C 2523/42* (2013.01); *C07C 2523/62* (2013.01); *C07C 2529/74* (2013.01); *C07C 2529/76* (2013.01)

(58) Field of Classification Search
CPC .................................. C07C 67/08; C07C 5/367
See application file for complete search history.

(56) References Cited

U.S. PATENT DOCUMENTS

| | | |
|---|---|---|
| 2,520,084 A | 8/1950 | Dazzi |
| 3,296,065 A | 1/1967 | O'Brien et al. |
| 3,842,040 A | 10/1974 | Browne et al. |
| 3,842,041 A | 10/1974 | Browne et al. |
| 3,928,481 A | 12/1975 | Suggitt |
| 3,928,484 A | 12/1975 | Suggitt |
| 3,962,362 A * | 6/1976 | Suggitt .................. 585/252 |
| 4,123,470 A | 10/1978 | Murtha |
| 4,218,572 A | 8/1980 | Dolhyj et al. |
| 4,263,457 A | 4/1981 | Takeda et al. |
| 4,294,976 A | 10/1981 | Itatani et al. |
| 4,463,207 A | 7/1984 | Johnson |
| 5,001,296 A | 3/1991 | Howley et al. |
| 5,138,022 A | 8/1992 | Mang et al. |
| 6,037,513 A | 3/2000 | Chang et al. |
| 6,103,919 A | 8/2000 | Schiraldi et al. |
| 6,274,756 B1 | 8/2001 | Caers et al. |
| 6,355,711 B1 | 3/2002 | Godwin et al. |
| 6,433,236 B1 | 8/2002 | Schiraldi et al. |
| 6,482,972 B1 | 11/2002 | Bahrmann et al. |
| 6,730,625 B1 | 5/2004 | Chang et al. |
| 6,740,254 B2 | 5/2004 | Zhou et al. |
| 6,777,514 B2 | 8/2004 | Patil et al. |
| 7,297,738 B2 | 11/2007 | Gosse et al. |
| 8,829,093 B2 | 9/2014 | Dakka et al. |
| 2005/0215433 A1 | 9/2005 | Benitez et al. |
| 2006/0247461 A1 | 11/2006 | Schlosberg et al. |
| 2008/0242895 A1 | 10/2008 | Godwin et al. |
| 2009/0299111 A1 * | 12/2009 | Kanbara et al. .................. 585/23 |
| 2010/0159177 A1 | 6/2010 | Dakka et al. |
| 2011/0151162 A1 | 6/2011 | Dakka et al. |
| 2011/0184105 A1 | 7/2011 | Dakka et al. |

(Continued)

FOREIGN PATENT DOCUMENTS

| | | |
|---|---|---|
| JP | 1996-20548 | 1/1996 |
| JP | 8020548 | 1/1996 |

(Continued)

OTHER PUBLICATIONS

Clary et al., "*A Green, One-Pot Route to the Biphenyldicarboxylic Acids: Useful Intermediates in Polymer Synthesis*," International Journal of Organic Chemistry, Jun. 2013, vol. 3, No. 2, pp. 143-147.

Ennis et al., "*Multikilogram-Scale Synthesis of a Biphenyl Carboxylic Acid Derivative Using a Pd/C-Mediated Suzuki Coupling Approach*," Organic Process 1999, 3(4), pp. 248-252.

Khromov et al., "*Catalytic Conversion Of 1,1'-Dimethyldicyclohexyl And 1-Methyl-1-Phenyl-Cyclohexane On Platinum Catalysts At Elevated Hydrogen Pressures And Temperatures*," Vestnik Moskovskogo Universiteta, Seriya 2: Khimiya (1965), 20(1), 51-5, (English Abstract Only).

Mukhopadhyay et al., "*Tandem One-Pot Palladium-Catalyzed Reductive and Oxidative Coupling of Benzene and Chlorobenzene*," Journal of Organic Chemistry (2000), 65(10), pp. 3107-3110.

(Continued)

*Primary Examiner* — Yong Chu
*Assistant Examiner* — Ana Z Muresan

(57) ABSTRACT

In a process for producing a methyl-substituted biphenyl compound, at least one methyl-substituted cyclohexylbenzene compound of the formula:

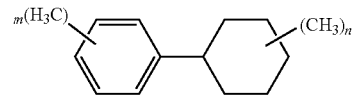

is contacted with a dehydrogenation catalyst under conditions effective to produce a dehydrogenation reaction product comprising at least one methyl-substituted biphenyl compound, wherein each of m and n is independently an integer from 1 to 3 and wherein the dehydrogenation catalyst comprises (i) an element or compound thereof from Group 10 of the Periodic Table of Elements and (ii) tin or a compound thereof.

39 Claims, 2 Drawing Sheets

(56) References Cited

U.S. PATENT DOCUMENTS

| | | | |
|---|---|---|---|
| 2011/0215433 | A1 | 9/2011 | Kokubun |
| 2012/0108726 | A1 | 5/2012 | Godwin et al. |
| 2012/0108874 | A1 | 5/2012 | Gralla et al. |
| 2012/0283494 | A1* | 11/2012 | Smith et al. .............. 585/252 |
| 2014/0212666 | A1 | 7/2014 | Dakka et al. |
| 2014/0272626 | A1 | 9/2014 | Berlowitz et al. |
| 2014/0275605 | A1 | 9/2014 | Dakka et al. |
| 2014/0275606 | A1 | 9/2014 | Bai et al. |
| 2014/0275607 | A1 | 9/2014 | Dakka et al. |
| 2014/0275609 | A1 | 9/2014 | Dakka et al. |
| 2014/0315021 | A1 | 10/2014 | Naert et al. |
| 2014/0316155 | A1 | 10/2014 | Dakka et al. |
| 2014/0323782 | A1 | 10/2014 | Chen et al. |
| 2014/0378697 | A1 | 12/2014 | de Smit et al. |
| 2015/0080545 | A1 | 3/2015 | Dakka et al. |
| 2015/0080546 | A1 | 3/2015 | Dakka et al. |

FOREIGN PATENT DOCUMENTS

| | | |
|---|---|---|
| JP | 08-099914 | 4/1996 |
| SU | 412182 | 1/1974 |
| WO | 99/32427 | 7/1999 |
| WO | 03/029339 | 4/2003 |
| WO | 2004/046078 | 6/2004 |
| WO | WO 2007/013469 | 2/2007 |
| WO | WO 2010/138248 | 12/2010 |
| WO | 2011/096989 | 8/2011 |
| WO | WO 2011/096993 | 8/2011 |
| WO | 2012/082407 | 6/2012 |
| WO | WO 2014/159094 | 10/2014 |
| WO | WO 2014/159104 | 10/2014 |

OTHER PUBLICATIONS

U.S. Appl. No. 61/203,626, filed Dec. 24, 2008, Dakka et al.
U.S. Appl. No. 61/040,480, filed Mar. 28, 2008, Godwin et al.
U.S. Appl. No. 61/781,116, filed Mar. 14, 2013, Bai et al.
Cheng, J.C. et al., "*Direct Alkylation of Aromatic Hydrocarbons with n-Paraffin*", Mobil Technology Company, SRC Progress Memo 97-310-006, Dec. 1, 1997, pp. 1-43.
Godwin, A.D. et al, "*Plasticizers*", Applied Polymer Science 21$^{st}$ Century, 2000, pp. 157-175.
Kulev, et al., "*Esters of diphenic acid and their plasticizing properties*", Izvestiya Tomskogo Politekhnicheskogo Instituta, 1961, 111. (English abstract only).
Shioda, et al., "*Synthesis of dialkyl diphenates and their properties*", Yuki Gosei Kagaku Kyokaishi, 1959, 17. (English abstract only).
Stevenson, S.A. et al., "*Conversion of Benzene to Phenylcyclohexane over a Tungsten/Zirconia Catalyst*", Mobil Technology Company, SRC Progress Memo 97M-0392, May 7, 1997, pp. 1-25.
Zhang, W. et al. "*Automation of Fluorous Solid-Phase Extraction for Parallel Synthesis*", J. Comb. Chem. (2006) pp. 890-896.
Lagidze et al., "*Analysis of Substances Produced By Reaction Between Aluminum Chloride and Diphenyl In Dearomatized Ligroin,*" V. I. Lein-n Georgian Polytechnic Institute (1968), No. 2 (122), pp. 36-44. (English Translation).
U.S. Appl. No. 13/316,745, Dec. 12, 2011, Patil et al.
U.S. Appl. No. 14/164,889, Jan. 27, 2014, Dakka et al.
U.S. Appl. No. 14/201,173, Mar. 7, 2014, Dakka et al.
U.S. Appl. No. 14/201,224, Mar. 7, 2014, Dakka et al.
U.S. Appl. No. 14/201,226, Mar. 7, 2014, Bai et al.
U.S. Appl. No. 14/201,284, Mar. 7, 2014, Dakka et al.
U.S. Appl. No. 14/201,287, Mar. 7, 2014, Dakka et al.
U.S. Appl. No. 14/480,363, Sep. 8, 2014, Dakka et al.
U.S. Appl. No. 14/486,945, Sep. 15, 2014, Dobin et al.
U.S. Appl. No. 14/516,239, Oct. 16, 2014, Dakka et al.
U.S. Appl. No. 14/527,480, Oct. 29, 2014, Patil et al.
U.S. Appl. No. 61/577,900, Dec. 20, 2011, Dakka et al.
U.S. Appl. No. 61/781,109, Mar. 14, 2013, Dakka et al.
U.S. Appl. No. 61/781,129, Mar. 14, 2014, Dakka et al.
U.S. Appl. No. 61/781,137, Mar. 14, 2014, Dakka et al.
U.S. Appl. No. 61/781,728, Mar. 14, 2014, Dakka et al.
U.S. Appl. No. 62/012,024, Jun. 13, 2014, Salciccioli et al.
U.S. Appl. No. 62/012,037, Jun. 13, 2014, Dakka et al.
U.S. Appl. No. 62/026,889, Jul. 21, 2014, Mohr et al.
U.S. Appl. No. 62/068,144, Oct. 24, 2014, Dakka et al.
U.S. Appl. No. 62/094,218, Dec. 19, 2014, Salciccioli et al.
U.S. Appl. No. 62/137,996, Mar. 25, 2015, Salciccioli et al.
U.S. Appl. No. 62/138,179, Mar. 25, 2015, Evans et al.
U.S. Appl. No. 62/140,723, Mar. 31, 2015, Salciccioli et al.
Bandyopadhyay et al., "*Transalkylation of cumene with toluene over zeolite Beta,*" Applied Catalysis A: General, 1996, vol. 135(2), pp. 249-259.
Bandyopadhyay et al., "*Transalkylation reaction—An alternative route to produce industrially important intermediates such as cymene,*" Catalysis Today, 1998, vol. 44, pp. 245-252.
Borodina et al., "Hydroalkylation of Benzene and Ethylbenzene over Metal-Containing Zeolite Catalysts," Petroleum Chemistry, 2009, vol. 49(1), pp. 66-73.
Guo, et al., "*Reactivity of 4,4'—Dimethylbiphenyl with Methanol over modified HZSM-5 Catalysts,*" PrePrints—American Chemical Society, Division of Petroleum Chemistry, 2003, vol. 48(4), pp. 280-282.
Izard, "Effect of Chemical Structure on Physical Properties of Isomeric Polyesters," Journal of Polymer Science, 1952, vol. 9(1), 35-39.
Krigbaum et al., "Aromatic Polyesters Forming Thermotropic Smectic Mesophases," Journal of Polymer Science, Part C, Polymer Letters Edition, 1982, vol. 20(2), pp. 109-115.
Lu et al., "Selective Hydrogenation of Single Benzene Ring in Biphenyl Catalyzed by Skeletal Ni," ChemCatChem., 2009, vol. 1(3), pp. 369-371.
Mavrodinova et al., "Transalkylation of toluene with cumene over zeolites Y dealuminated in solid-state, Part I. Effect of the alteration of Broensted acidity," Applied Catalysis A: General, 2003, vol. 248, pp. 181-196.
Mavrodinova et al., "Transalkylation of toluene with cumene over zeolites Y dealuminated in solid-state Part II. Effect of the introduced Lewis acid sites," Applied Catalysis A: General, 2003, vol. 248, pp. 197-209.
Meurisse et al., "Polymers with Mesogenic Elements and Flexible Spacers in the Main Chain: Aromatic-Aliphatic Polyesters," British Polymer Journal, 1981, vol. 13(2), pp. 55-63.
Roux et al., "Critically Evaluated Thermochemical Properties of Polycyclic Aromatic Hydrocarbons," Journal of Physical and Chemical Reference Data, 2008, vol. 37(4), pp. 1855-1996.
Sherman et al., "Dimethylbiphenyls from toluene," American Chemical Society, Chemical Innovation, 2000, pp. 25-30.
Sinfelt, "The turnover frequency of methylcyclohexane dehydrogenation to toluene on a Pt reforming catalyst," Journal of Molecular Catalysis A: Chemical, 2000, vol. 163, pp. 123-128.
Sinfelt et al., "Kinetics of Methylcyclohexane Dehydrogenation Over PT-Al$_2$O$_3$," Journal of Physical Chemistry, 1960, vol. 64(10), 1559-1562.
Singh, et. al, "*Studies on Isomer Distribution in the Products Obtained by Friedekrafis Alkylation of Toluene with Cyclic Electrophiles,*" National Academy Science Letters, 1983, vol. 6(10), pp. 321-325.

\* cited by examiner

METHYL-SUBSTITUTED BIPHENYL COMPOUNDS, THEIR PRODUCTION AND THEIR USE IN THE MANUFACTURE OF PLASTICIZERS

PRIORITY

This application claims the benefit of and priority to Provisional Application No. 61/781,116, filed Mar. 14, 2013.

FIELD

The disclosure relates to methyl-substituted biphenyl compounds, their production and their use in the manufacture of plasticizers.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

The most important chemical class of plasticizers is phthalic acid esters, which accounted for about 84% worldwide of PVC plasticizer usage in 2009.

Others are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, U.S. Patent Publication No. 2006-0247461, and U.S. Pat. No. 7,297,738.

Others also include esters based on benzoic acid (see, for instance, U.S. Pat. No. 6,740,254) and polyketones, such as described in U.S. Pat. No. 6,777,514; and U.S. Patent Publication No. 2008-0242895. Epoxidized soybean oil, which has much longer alkyl groups ($C_{16}$ to $C_{18}$), has been tried as a plasticizer, but is generally used as a PVC stabilizer. Stabilizers are used in much lower concentrations than plasticizers. U.S. Patent Publication No. 2010-0159177 discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins and that can be made with a high throughput.

For example, in an article entitled "Esters of diphenic acid and their plasticizing properties", Kulev et al., *Izvestiya Tomskogo Politekhnicheskogo Instituta* (1961) 111, disclose that diisoamyl diphenate, bis(2-ethylhexyl)diphenate and mixed heptyl, octyl and nonyl diphenates can be prepared by esterification of diphenic acid, and allege that the resultant esters are useful as plasticizers for vinyl chloride. Similarly, in an article entitled "Synthesis of dialkyl diphenates and their properties", Shioda et al., *Yuki Gosei Kagaku Kyokaishi* (1959), 17, disclose that dialkyl diphenates of $C_1$ to $C_8$ alcohols, said to be useful as plasticizers for poly(vinyl chloride), can be formed by converting diphenic acid to diphenic anhydride and esterifying the diphenic anhydride. However, since these processes involve esterification of diphenic acid or anhydride, they necessarily result in 2,2'-substituted diesters of diphenic acid. Generally, such diesters having substitution on the 2-carbons have proven to be too volatile for use as plasticizers.

An alternative method of producing dialkyl diphenate esters having an increased proportion of the less volatile 3,3', 3,4' and 4,4' diesters has now been developed. In particular, it has been found that dimethyl biphenyl compounds containing significant amounts of the 3,3'-dimethyl, the 3,4'-dimethyl and the 4,4'-dimethyl isomers can be economically produced by hydroalkylation of toluene and/or xylene followed by dehydrogenation of the resulting (methylcyclohexyl)toluene and/or (dimethylcyclohexyl)xylene product. The resultant mixture can then be used as a precursor in the production of biphenylester-based plasticizers by, for example, oxidixing the methyl-substituted biphenyl compounds to convert at least one of the methyl groups to a carboxylic acid group and then esterifying the carboxylic acid group(s) with an alcohol, such as an oxo alcohol. One important step in this overall process is the dehydrogenation reaction and, in particular, it has now been found that the addition of tin to the dehydrogenation catalyst significantly improves the selectivity to the desired dimethyl biphenyl isomer mixture.

SUMMARY

Accordingly, in one aspect, the present disclosure relates to a process for producing a methyl-substituted biphenyl compound, the process comprising:

(a) contacting at least one methyl-substituted cyclohexylbenzene compound of the formula:

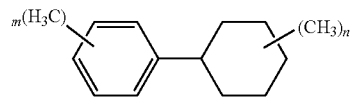

with a dehydrogenation catalyst under conditions effective to produce a dehydrogenation reaction product comprising at least one methyl-substituted biphenyl compound wherein each of m and n is independently an integer from 1 to 3 and wherein the dehydrogenation catalyst comprises (i) an element or compound thereof from Group 10 of the Periodic Table of Elements and (ii) tin or a compound thereof.

In one embodiment, each of m and n is 1 and the dehydrogenation reaction product comprises less than 10 wt % of monomethyl-substituted biphenyl compounds.

In a further aspect, the present disclosure relates to a process for producing methyl-substituted biphenyl compounds, the process comprising:

(a) contacting a feed comprising at least one aromatic hydrocarbon selected from the group consisting of toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes; and (b) dehydrogenating at least part of the hydroalkylation reaction product in the presence of a dehydrogenation catalyst under conditions effective to produce a dehydrogenation reaction product comprising a mixture of methyl-substituted biphenyl compounds, wherein the dehydrogenation catalyst comprises (i) an element or compound thereof from Group 10 of the Periodic Table of Elements and (ii) tin or a compound thereof.

In one embodiment, the aromatic hydrocarbon is toluene and the dehydrogenation reaction product comprises less than 5 wt % of fluorene and methylfluorenes combined.

In yet a further aspect, the present disclosure relates to a process for producing biphenyl esters, the process comprising:

(a) contacting a feed comprising at least one aromatic hydrocarbon selected from the group consisting of toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes; and (b) dehydrogenating at least part of the hydroalkylation reaction product in the presence of a dehydrogenation catalyst under conditions effective to produce a dehydrogenation reaction product comprising a mixture of methyl-substituted biphenyl compounds, wherein the dehydrogenation catalyst comprises (i) an element or compound thereof from Group 10 of the Periodic Table of Elements and (ii) tin or a compound thereof;

(c) contacting at least part of the dehydrogenation reaction product with an oxygen source under conditions effective to convert at least part of the methyl-substituted biphenyl compounds to biphenyl carboxylic acids; and (d) reacting the biphenyl carboxylic acids with one or more $C_4$ to $C_{14}$ alcohols under conditions effective to produce biphenyl esters.

DETAILED DESCRIPTION OF THE EMBODIMENTS

Figure 1:
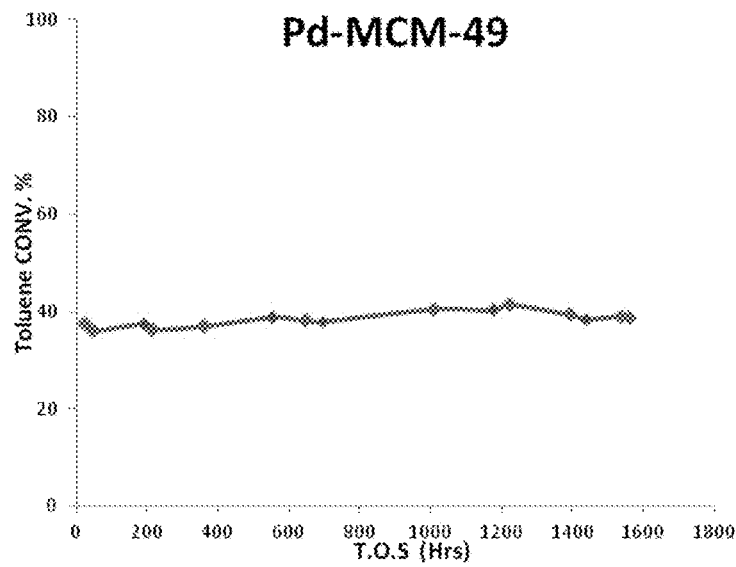
FIG. 1 is a graph of toluene conversion against time on stream (TOS) in the hydroalkylation of toluene over the Pd-MCM-49 catalyst of Example 1.

Described herein is a process for producing methyl substituted biphenyl compounds useful as precursors in the manufacture of biphenyl ester plasticizers. As discussed below, the process involves the catalytic hydroalkylation of toluene and/or xylene to produce methyl-substituted cyclohexylbenzene compounds followed by the catalytic dehydrogenation of at least part of the hydroalkylation reaction product. In particular, the present process employs a dehydrogenation catalyst comprising (i) an element or compound thereof from Group 10 of the Periodic Table of Elements and (ii) tin or a compound thereof. Thus it has been found that the addition of the addition of tin to the dehydrogenation catalyst significantly improves the selectivity to the desired methyl substituted biphenyl compounds.

As used herein, the numbering scheme for the Periodic Table Groups is the new notation as disclosed in Chemical and Engineering News, 63(5), 27 (1985).

Hydroalkylation of Toluene and/or Xylene

Hydroalkylation is a two-stage catalytic reaction in which an aromatic compound is partially hydrogenated to produce a cyclic olefin, which then reacts, in situ, with the aromatic compound to produce a cycloalkylaromatic product. In the present process, the aromatic feed comprises toluene and/or xylene and the cycloalkylaromatic product comprises a mixture of (methylcyclohexyl)toluene and/or (dimethylcyclohexyl)xylene isomers. In the case of toluene, the desired reaction may be summarized as follows:

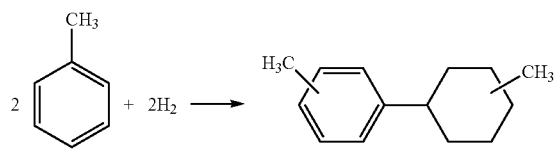

Among the competing reactions is further hydrogenation of the cyclic olefin intermediate and/or the cycloalkylaromatic product to produce fully saturated rings. In the case of toluene as the hydroalkylation feed, further hydrogenation can produce methylcyclohexane and dimethylbicyclohexane compounds. Although these by-products can be converted back to feed (toluene) and to the product ((methylcyclohexyl)toluene and dimethylbiphenyl) via dehydrogenation, this involves an endothermic reaction requiring high temperatures (>375° C.) to obtain high conversion. This not only makes the reaction costly but can also lead to further by-product formation and hence yield loss. It is therefore desirable to employ a hydroalkylation catalyst that exhibits low selectivity towards the production of fully saturated rings.

Another competing reaction is dialkylation in which the (methylcyclohexyl)toluene product reacts with further methylcyclohexene to produce di(methylcyclohexyl)toluene. Again this by-product can be converted back to (methylcyclohexyl)toluene, in this case by transalkylation. However, this process requires the use of an acid catalyst at temperatures above 160° C. and can lead to the production of additional by-products, such as di(methylcyclopentyl)toluenes, cyclohexylxylenes and cyclohexylbenzene. It is therefore desirable to employ a hydroalkylation catalyst that exhibits low selectivity towards di(methylcyclohexyl)toluene and other heavy by-products.

The catalyst employed in the hydroalkylation reaction is a bifunctional catalyst comprising a hydrogenation component and a solid acid alkylation component, typically a molecular sieve. The catalyst may also include a binder such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the catalyst, although suitable metals include palladium, ruthenium, nickel, zinc, tin, and cobalt, with palladium being particularly advantageous. In certain embodiments, the amount of hydrogenation metal present in the catalyst is between about 0.05 and about 10 wt %, such as between about 0.1 and about 5 wt %, of the catalyst.

In one embodiment, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

In another, more preferred embodiment, the solid acid alkylation component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In addition to the toluene and/or xylene and hydrogen, a diluent, which is substantially inert under hydroalkylation conditions, may be supplied to the hydroalkylation reaction. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

In one embodiment, the aromatic feed to the hydroalkylation reaction also includes benzene and/or one or more alkylbenzenes different from toluene and xylene. Suitable alkylbenzenes may have one or more alkyl groups with up to 4 carbon atoms and include, by way of example, ethylbenzene, cumene, and unseparated $C_6$-$C_8$ or $C_7$-$C_8$ or $C_7$-$C_9$ streams.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed is typically from about 0.15:1 to about 15:1.

In the present process, it is found that MCM-22 family molecular sieves are particularly active and stable catalysts for the hydroalkylation of toluene or xylene. In addition, catalysts containing MCM-22 family molecular sieves exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it is found that the hydroalkylation reaction product may comprise:

at least 60 wt %, such as at least 70 wt %, for example at least 80 wt % of the 3,3, 3,4, 4,3 and 4,4-isomers of (methylcyclohexyl)toluene based on the total weight of all the (methylcyclohexyl)toluene isomers;

less than 30 wt % of methylcyclohexane and less than 2% of dimethylbicyclohexane compounds;

and less than 1 wt % of compounds containing in excess of 14 carbon atoms.

Similarly, with a xylene feed, the hydroalkylation reaction product may comprise less than 1 wt % of compounds containing in excess of 16 carbon atoms.

By way of illustration, the 3,3, 3,4 4,3 and 4,4-isomers of (methylcyclohexyl)toluene are illustrated in formulas F1 to F4, respectively:

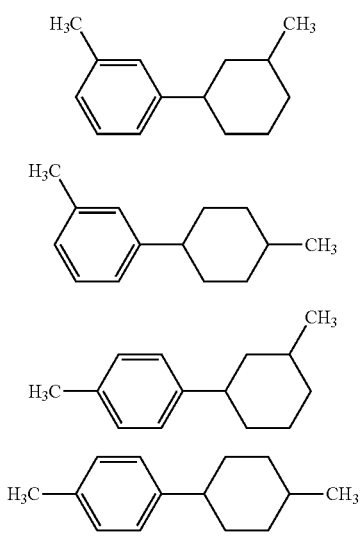

In contrast, when the methyl group is located in the 1-position (quaternary carbon) on the cyclohexyl ring, ring isomerization can occur forming (dimethylcyclopentyl)toluene and (ethylcyclopentyl)toluene which, on dehydrogenation, will generate diene by-products which are difficult to separate from the desired product and will also inhibit the subsequent oxidation reaction. In the oxidation and esterification steps, different isomers have different reactivity. Thus, para-isomers are more reactive than meta-isomers which are more reactive than ortho-isomers. Also in the dehydrogenation step, the presence of a methyl group in the 2 position on either the cyclohexyl or phenyl ring is a precursor for the formation of fluorene and methyl fluorene. Fluorene is difficult to separate from the dimethylbiphenyl product and causes problems in the oxidation step and also in the plasticizers performance. It is therefore advantageous to minimize the formation of isomers which have a methyl group in the ortho, 2 and benzylic positions.

Dehydrogenation of Hydroalkylation Product

The major components of the hydroalkylation reaction effluent are (methylcyclohexyl)toluenes and/or (dimethylcyclohexyl)xylenes, unreacted aromatic feed (toluene and/or xylene) and fully saturated single ring by-products (methylcyclohexane and dimethylcyclohexane). The unreacted feed and light by-products can readily be removed from the reaction effluent by, for example, distillation. The unreacted feed can then be recycled to the hydroalkylation reactor, while the saturated by-products can be dehydrogenated to produce additional recycleable feed.

The remainder of the hydroalkylation reaction effluent, composed mainly of (methylcyclohexyl)toluenes and/or (dimethylcyclohexyl)xylenes, is then catalytically dehydrogenated to produce the corresponding methyl-substituted biphenyl compounds. The catalyst employed in the dehydrogenation process comprises (i) an element or compound from Group 10 of the Periodic Table of Elements, for example platinum, and (ii) tin or a compound of tin, both mounted on a refractory support, such as silica, alumina or carbon nanotubes. In one embodiment, the Group 10 element is present in amount from 0.1 to 5 wt % of the catalyst and the tin is present in amount from 0.05 to 2.5 wt % of the catalyst.

The dehydrogenation is conveniently conducted at a temperature from about 200° C. to about 600° C. and a pressure from about 100 kPa to about 3550 kPa (atmospheric to about 500 psig) in the presence of dehydrogenation catalyst.

Particularly using an MCM-22 family-based catalyst for the upstream hydroalkylation reaction, the product of the dehydrogenation step comprises methyl-substituted biphenyl compounds in which the concentration of the 3,3-, 3,4- and 4,4-dimethyl isomers is at least 50 wt %, such as at least 60 wt %, for example at least 70 wt % based on the total weight of methyl-substituted biphenyl isomers. In addition, the product may contain less than 10 wt %, such as less than 5 wt %, for example less than 3 wt % of methyl biphenyl compounds and less than 5 wt %, such as less than 3 wt %, for example less than 1 wt % of fluorene and methyl fluorenes combined.

Production of Biphenyl Esters

The methyl-substituted biphenyl compounds produced by the dehydrogenation reaction can readily be converted ester plasticizers by a process comprising oxidation to produce the corresponding carboxylic acids followed by esterification with an alcohol.

The oxidation can be performed by any process known in the art, such as by reacting the methyl-substituted biphenyl compounds with an oxidant, such as oxygen, ozone or air, or any other oxygen source, such as hydrogen peroxide, in the presence of a catalyst at temperatures from 30° C. to 300° C., such as from 60° C. to 200° C. Suitable catalysts comprise Co or Mn or a combination of both metals.

The resulting carboxylic acids can then be esterified to produce biphenyl ester plasticizers by reaction with one or more $C_4$ to $C_{14}$ alcohols. Suitable esterification conditions are well-known in the art and include, but are not limited to, temperatures of 0-300° C. and the presence or absence of homogeneous or heterogeneous esterification catalysts, such as Lewis or Bronsted acid catalysts. Suitable alcohols are "oxo-alcohols", by which is meant an organic alcohol, or mixture of organic alcohols, which is prepared by hydroformylating an olefin, followed by hydrogenation to form the alcohols. Typically, the olefin is formed by light olefin oligomerization over heterogeneous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. Another source of olefins used in the OXO process are through the oligomerization of ethylene, producing mixtures of predominately straight chain alcohols with lesser amounts of lightly branched alcohols.

The biphenyl ester plasticizers of the present application find use in a number of different polymers, such as vinyl chloride resins, polyesters, polyurethanes, ethylene-vinyl acetate copolymers, rubbers, poly(meth)acrylics and mixtures thereof.

The invention will now be more particularly described with reference to the accompanying drawings and the following non-limiting Examples.

Example 1

Synthesis of 0.3% Pd/MCM-49 Hydroalkylation Catalyst 80 parts MCM-49 zeolite crystals are combined with 20 parts pseudoboehmite alumina, on a calcined dry weight basis. The MCM-49 and pseudoboehmite alumina dry powder is placed in a muller and mixed for about 10 to 30 minutes. Sufficient water and 0.05% polyvinyl alcohol is added to the MCM-49 and alumina during the mixing process to produce an extrudable paste. The extrudable paste is formed into a ¹⁄₂₀ inch (0.13 cm) quadrulobe extrudate using an extruder and the resulting extrudate is dried at a temperature ranging from 250° F. to 325° F. (120° C. to 163° C.). After drying, the dried extrudate is heated to 1000° F. (538° C.) under flowing nitrogen. The extrudate is then cooled to ambient temperature and humidified with saturated air or steam.

After the humidification, the extrudate is ion exchanged with 0.5 to 1 N ammonium nitrate solution. The ammonium nitrate solution ion exchange is repeated. The ammonium nitrate exchanged extrudate is then washed with deionized water to remove residual nitrate prior to calcination in air. After washing the wet extrudate, it is dried. The exchanged and dried extrudate is then calcined in a nitrogen/air mixture to a temperature 1000° F. (538° C.). Afterwards, the calcined extrudate is cooled to room temperature. The 80% MCM-49, 20% $Al_2O_3$ extrudate was incipient wetness impregnated with a palladium (II) chloride solution (target: 0.30% Pd) and then dried overnight at 121° C. The dried catalyst was calcined in air at the following conditions: 5 volumes air per volume catalyst per minute, ramp from ambient to 538° C. at 1° C./min and hold for 3 hours.

Example 2

Synthesis of 0.3% Pd/Beta Hydroalkylation Catalyst 80 parts beta zeolite crystals are combined with 20 parts pseudoboehmite alumina, on a calcined dry weight basis. The beta and pseudoboehmite are mixed in a muller for about 15 to 60 minutes. Sufficient water and 1.0% nitric acid is added during the mixing process to produce an extrudable paste. The extrudable paste is formed into a 1/20 inch quadrulobe extrudate using an extruder. After extrusion, the 1/20th inch quadrulobe extrudate is dried at a temperature ranging from 250° F. to 325° F. (120° C. to 163° C.). After drying, the dried extrudate is heated to 1000° F. (538° C.) under flowing nitrogen and then calcined in air at a temperature of 1000° F. (538° C.). Afterwards, the calcined extrudate is cooled to room temperature. The 80% Beta, 20% $Al_2O_3$ extrudate was incipient wetness impregnated with a tetraammine palladium (II) nitrate solution (target: 0.30% Pd) and then dried overnight at 121° C. The dried catalyst was calcined in air at the following conditions: 5 volumes air per volume catalyst per minute, ramp from ambient to 538° C. at 1° C./min and hold for 3 hours.

Example 3

Hydroalkylation Catalyst Testing

Each of the catalyst of Examples 1 to 4 was then tested in the hydroalkylation of a toluene feed using the reactor and process described below.

The reactor comprised a stainless steel tube having an outside diameter of: 3/8 inch (0.95 cm), a length of 20.5 inch (52 cm) and a wall thickness of 0.35 inch (0.9 cm). A piece of stainless steel tubing having a length of 8¾ inch (22 cm) and an outside diameter of: 3/8 inch (0.95 cm) and a similar length of ¼ inch (0.6 cm) tubing of were used in the bottom of the reactor (one inside of the other) as a spacer to position and support the catalyst in the isothermal zone of the furnace. A ¼ inch (0.6 cm) plug of glass wool was placed on top of the spacer to keep the catalyst in place. A ⅛ inch (0.3 cm) stainless steel thermo-well was placed in the catalyst bed to monitor temperature throughout the catalyst bed using a movable thermocouple.

The catalyst was sized to 20/40 sieve mesh or cut to 1:1 length to diameter ratio, dispersed with quartz chips (20/40 mesh) then loaded into the reactor from the top to a volume of 5.5 cc. The catalyst bed typically was 15 cm in length. The remaining void space at the top of the reactor was filled with quartz chips, with a ¼plug of glass wool placed on top of the catalyst bed being used to separate quartz chips from the catalyst. The reactor was installed in a furnace with the catalyst bed in the middle of the furnace at a pre-marked isothermal zone. The reactor was then pressure and leak tested typically at 300 psig (2170 kPa).

The catalyst was pre-conditioned in situ by heating to 25° C. to 240° C. with $H_2$ flow at 100 cc/min and holding for 12 hours. A 500 cc ISCO syringe pump was used to introduce a chemical grade toluene feed to the reactor. The feed was pumped through a vaporizer before flowing through heated lines to the reactor. A Brooks mass flow controller was used to set the hydrogen flow rate. A Grove "Mity Mite" back pressure controller was used to control the reactor pressure typically at 150 psig (1135 kPa). GC analyses were taken to verify feed composition. The feed was then pumped through the catalyst bed held at the reaction temperature of 120° C. to 180° C. at a WHSV of 2 and a pressure of 15-200 psig (204-1480 kPa). The liquid products exiting the reactor flowed through heated lines routed to two collection pots in series, the first pot being heated to 60° C. and the second pot cooled with chilled coolant to about 10° C. Material balances were taken at 12 to 24 hrs intervals. Samples were taken and diluted with 50% ethanol for analysis. An Agilent 7890 gas chromatograph with FID detector was used for the analysis. The non-condensable gas products were routed to an on line HP 5890 GC.

The analysis is done on an Agilent 7890 GC with 150 vial sample tray.
Inlet Temp: 220° C.
Detector Temp: 240° C. (Col+make up=constant)
Temp Program: Initial temp 120° C. hold for 15 min., ramp at 2° C./min to 180° C., hold 15 min; ramp at 3° C./min. to 220° C. and hold till end.
Column Flow: 2.25 ml/min. (27 cm/sec); Split mode, Split ratio 100:1 Injector: Auto sampler (0.2 μl).
Column Parameters:
Two columns joined to make 120 Meters (coupled with Agilent ultimate union, deactivated.
Column # Front end: Supelco β-Dex 120; 60 m×0.25 mm×0.25 μm film joined to Column #2 back end: γ-Dex 325: 60 m×0.25 mm×0.25 μm film.

Figure 2:
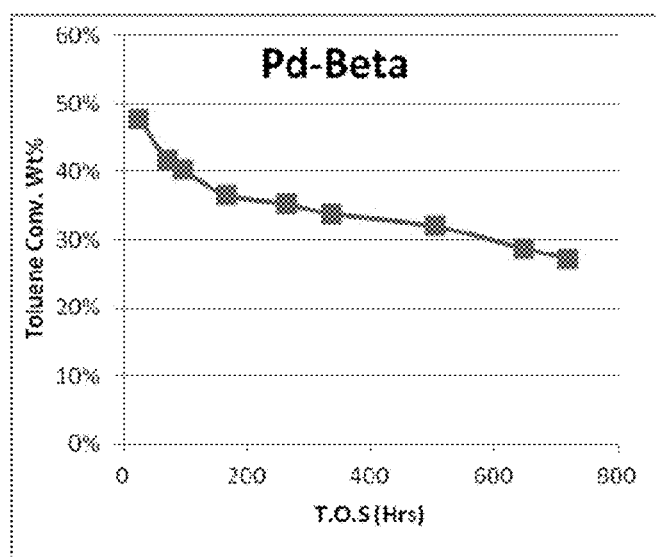
FIG. 2 is a graph of toluene conversion against time on stream (TOS) in the hydroalkylation of toluene over the Pd-beta catalyst of Example 2.

The results of the hydroalkylation testing are summarized in FIGS. 1 and 2 and in Table 1, in which MCM designates methylcyclohexane, DMCH designates dimethylbi(cyclohexane) and DMCHT designates di(methylcyclohexyl)toluene.

TABLE 1

| Example | Catalyst | Toluene conversion | Selectivity to MCH | Selectivity to DMBCH | Selectivity to DMCHT |
| --- | --- | --- | --- | --- | --- |
| 1 | 0.3% Pd?MCM49 | 37% | 23% | 1.40% | 0.5% |
| 2 | 0.3% Pd/Beta | 40% | 65% | 1.60% | 5.5% |

As can be seen from Table 1, the Pd/MCM-49 catalyst has much lower selectivity than the Pd/beta catalyst towards the production of the fully saturated by-products, methylcyclohexane and dimethylbi(cyclohexane) and to the production of dialkylate products. In addition, as shown in FIGS. 1 and 2, the Pd/MCM-49 catalyst was found to exhibit improved stability and catalyst life as compared with the Pd/beta catalyst.

Example 4

Production of 1% Pt/0.15% Sn/SiO$_2$ Dehydrogenation Catalyst

A 1% Pt/0.15% Sn/SiO$_2$ catalyst was prepared by incipient wetness impregnation, in which a ⅟₂₀" (1.2 mm) quadrulobe silica extrudate was initially impregnated with an aqueous solution of tin chloride and then dried in air at 121° C. The resultant tin-containing extrudates were then impregnated with an aqueous solution of tetraammine Pt nitrate and again dried in air at 121° C. The resultant product was calcined in air at 350° C. for 3 hours before being used in subsequent catalyst testing.

Example 5

Preparation of 1% Pt/Θ—Al$_2$O$_3$ Dehydrogenation Catalyst

θ-Al$_2$O$_3$ 2.5 mm trilobe extrudates were used as a support for Pt deposition. The support had a surface area of 126 m$^2$/g, a pore volume of 0.58 cm$^3$/g, and a pore size of 143 Å, measured by BET N$_2$ adsorption. Pt was added to θ-Al$_2$O$_3$ support by impregnating with aqueous solution of (NH$_3$)$_4$Pt(NO$_3$)$_2$. The Pt metal loading on the supports is adjusted at 1 wt %. After impregnating, the sample was placed in a glass dish at room temperature for 60 minutes to reach equilibrium. Then it was dried in air at 250° F. (120° C.) for 4 hrs and then calcined in a box furnace at 680° F. (360° C.) in air for 3 hrs. The furnace was ramped at 3° F./minute to the calcinations temperature and the air flow rate for the calcination was adjusted to 5 volume/volume catalyst/minute.

Example 6

Dehydrogenation Catalyst Testing

The catalysts of Examples 4 and 5 were used to perform dehydrogenation tests on the conversion products obtained in Example 3 from the Pd/MCM-49 and Pd/beta catalysts of Examples 1 and 2. In addition, the same tests were performed using a commercial 0.3 wt % Pt/Al$_2$O$_3$ dehydrogenation catalyst supplied by Akzo. The same reactor, catalyst and analytical configuration as described in Example 3 was used to perform dehydrogenation tests, except each dehydrogenation catalyst was pre-conditioned in situ by heating to 375° C. to 460° C. with H$_2$ flow at 100 cc/min and holding for 2 hours. In addition, in the dehydrogenation tests the catalyst bed was held at the reaction temperature of 375° C. to 460° C. at a WHSV of 2 and a pressure of 100 psig (790 kPa).

Figure 3:
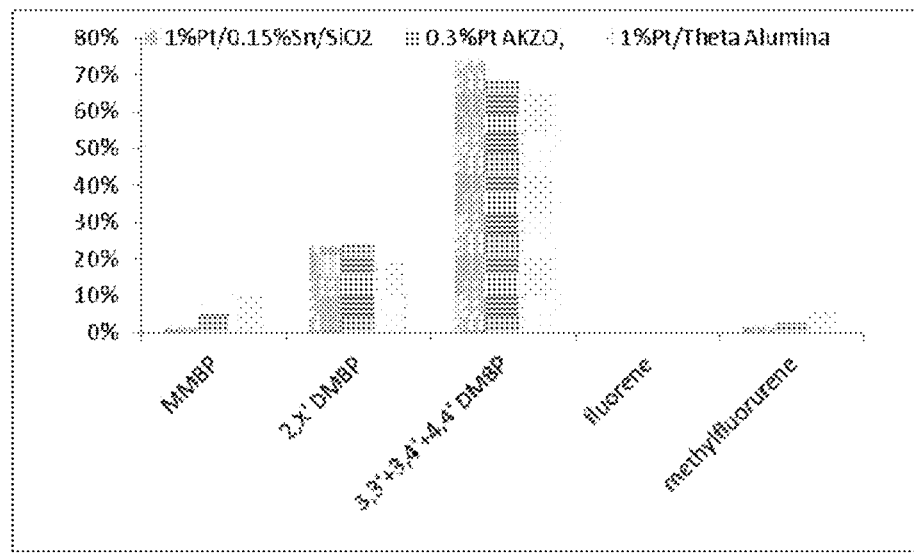
FIG. 3 is a bar graph comparing the composition of the products obtained using the various catalysts tested in Example 6 to dehydrogenate the product of the hydroalkylation of toluene over the Pd/MCM-49 catalyst of Example 1.
Figure 4:
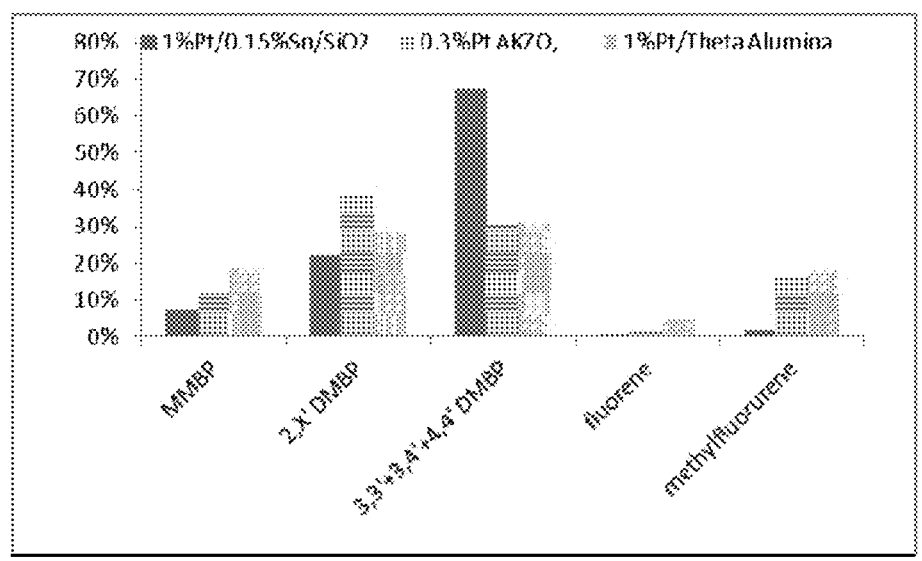
FIG. 4 is a bar graph comparing the composition of the products obtained using the various catalysts tested in Example 6 to dehydrogenate the product of the hydroalkylation of toluene over the Pd/zeolite beta catalyst of Example 2.

The results of the dehydrogenation testing are summarized in FIG. 3 for the hydroalkylation product of the Pd/MCM-49 catalyst and in FIG. 4 for the hydroalkylation product of the Pd/beta catalyst. The data clearly shows that dehydrogenation of the MCM-49 hydroalkylation products provides less mono methyl biphenyl, less of the 2',3 and 2',4 dimethyl biphenyl isomers which are the precursor for the formation of fluorene and methyl fluorene and much less the fluorene and methyl fluorene as compared with dehydrogenation of the zeolite beta hydroalkylation products. In addition, FIGS. 3 and 4 show that the tin-containing catalyst of Example 4 was much more selective to the desired 3',3, 3',4 and 4',4 dimethyl biphenyl products and made less monomethyl biphenyl, fluorene and methylfluorene as compared with the catalysts which had no tin.

While various embodiments have been described, it is to be understood that further embodiments will be apparent to those skilled in the art and that such embodiments are to be considered within the purview and scope of the appended claims. Such further embodiments include those defined in the following paragraphs:

A process for producing a methyl-substituted biphenyl compound, the process comprising:

(a) contacting at least one methyl-substituted cyclohexylbenzene compound of the formula:

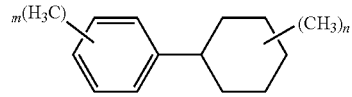

with a dehydrogenation catalyst under conditions effective to produce a dehydrogenation reaction product comprising at least one methyl-substituted biphenyl compound wherein each of m and n is independently an integer from 1 to 3, and preferably is 1, and wherein the dehydrogenation catalyst comprises (i) an element or compound thereof from Group 10 of the Periodic Table of Elements and (ii) tin or a compound thereof.

A process for producing methyl-substituted biphenyl compounds, the process comprising:

(a) contacting a feed comprising at least one aromatic hydrocarbon selected from the group consisting of toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes; and (b) dehydrogenating at least part of the hydroalkylation reaction product in the presence of a dehydrogenation catalyst under conditions effective to produce a dehydrogenation reaction product comprising a mixture of methyl-substituted biphenyl compounds, wherein the dehydrogenation catalyst comprises (i) an element or compound thereof from Group 10 of the Periodic Table of Elements and (ii) tin or a compound thereof.

The process of paragraph [0061], wherein the hydroalkylation catalyst comprises an acidic component and a hydrogenation component.

The process of paragraph [0062], wherein the acidic component of the hydroalkylation catalyst comprises a molecular sieve.

The process of paragraph [0063], wherein the molecular sieve is selected from the group consisting of BEA, FAU and MTW structure type molecular sieves, molecular sieves of the MCM-22 family and mixtures thereof.

The process of paragraph [0063] or [0064], wherein the molecular sieve comprises a molecular sieve of the MCM-22 family.

The process of any one of paragraphs [0062] to [0065], wherein the hydrogenation component of the hydroalkylation catalyst selected from the group consisting of palladium, ruthenium, nickel, zinc, tin, cobalt and compounds and mixtures thereof.

The process of any one of paragraphs [0061] to [0066], wherein the hydroalkylation conditions in the contacting (a) include a temperature from 100° C. to 400° C. and a pressure from 100 to 7,000 kPa.

The process of any one of paragraphs [0061] to [0067], wherein the molar ratio of hydrogen to aromatic feed supplied to the contacting (a) is from about 0.15:1 to about 15:1.

The process of any one of paragraphs [0061] to [0068], wherein the aromatic hydrocarbon is toluene and the hydroalkylation reaction product comprises less than 30 wt % of methylcyclohexane and less than 2% of dimethylbicyclohexane compounds.

The process of any one of paragraphs [0061] to [0069], wherein the aromatic hydrocarbon is toluene and the hydroalkylation reaction product comprises less than 1 wt % of compounds containing in excess of 14 carbon atoms.

The process of any one of paragraphs [0061] to [0071], wherein the feed further comprises benzene and/or at least one alkylbenzene different from toluene and xylene.

The process of any one of paragraphs [0060] to [0071], wherein the aromatic hydrocarbon is toluene and the dehydrogenation reaction product comprises less than 10 wt % of monomethyl-substituted biphenyl compounds.

The process of any one of paragraphs [0060] to [0072], wherein the aromatic hydrocarbon is toluene and the dehydrogenation reaction product comprises less than 5 wt % of fluorene and methylfluorenes combined.

The process of any one of paragraphs [0060] to [0073], wherein the dehydrogenation conditions in (b) include a temperature from 200° C. to 600° C. and a pressure from 100 kPa to 3550 kPa (atmospheric to 500 psig).

A process for producing biphenyl esters, the process comprising:
(i) contacting at least part of the methyl-substituted biphenyl compounds produced by the process of any one of paragraphs [0060] to [0074] with an oxygen source under conditions effective to convert at least part of the methyl-substituted biphenyl compounds to biphenyl carboxylic acids; and (ii) reacting the biphenyl carboxylic acids with one or more $C_4$ to $C_{14}$ alcohols under conditions effective to produce biphenyl esters.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

The invention claimed is:

1. A process for producing a methyl-substituted biphenyl compound, the process comprising:
   (a) contacting at least one methyl-substituted cyclohexylbenzene compound of the formula:

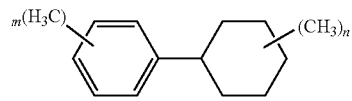

with a dehydrogenation catalyst under conditions effective to produce a dehydrogenation reaction product comprising at least one methyl-substituted biphenyl compound wherein each of m and n is independently an integer from 1 to 3 and wherein the dehydrogenation catalyst comprises (i) platinum and (ii) tin or a compound thereof wherein the hydrogenation product contains less than 10 wt % of methyl biphenyl compounds and less than 5 wt % of fluorene and methyl fluorenes combined.

2. The process of claim 1, wherein each of m and n is 1.

3. The process of claim 2, wherein the dehydrogenation reaction product comprises less than 10 wt % of monomethyl-substituted biphenyl compounds.

4. A process for producing methyl-substituted biphenyl compounds, the process comprising:
   (a) contacting a feed comprising at least one aromatic hydrocarbon selected from the group consisting of toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes; and
   (b) dehydrogenating at least part of the hydroalkylation reaction product in the presence of a dehydrogenation catalyst under conditions effective to produce a dehydrogenation reaction product comprising a mixture of methyl-substituted biphenyl compounds, wherein the dehydrogenation catalyst comprises (i) an element or compound thereof from Group 10 of the Periodic Table of Elements and (ii) tin or a compound thereof, wherein the hydroalkylation reaction product comprises at least 60 wt % of the 3,3, 3,4, 4,3 and 4,4-isomers of (methylcyclohexyl)toluene based on the total weight of all the (methylcyclohexyl)toluene isomers and less than 30 wt % of methylcyclohexane.

5. The process of claim 4, wherein the hydroalkylation catalyst comprises an acidic component and a hydrogenation component.

6. The process of claim 5, wherein the acidic component of the hydroalkylation catalyst comprises a molecular sieve.

7. The process of claim 6, wherein the molecular sieve is selected from the group consisting of BEA, FAU and MTW structure type molecular sieves, molecular sieves of the MCM-22 family and mixtures thereof.

8. The process of claim 6, wherein the molecular sieve comprises a molecular sieve of the MCM-22 family.

9. The process of claim 5, wherein the hydrogenation component of the hydroalkylation catalyst selected from the group consisting of palladium, ruthenium, nickel, zinc, tin, cobalt and compounds and mixtures thereof.

10. The process of claim 4, wherein the hydroalkylation conditions in the contacting (a) include a temperature from about 100° C. to about 400° C. and a pressure from about 100 to about 7,000 kPa.

11. The process of claim 4, wherein the molar ratio of hydrogen to aromatic feed supplied to the contacting (a) is from about 0.15:1 to about 15:1.

12. The process of claim 4, wherein the aromatic hydrocarbon is toluene and the hydroalkylation reaction product comprises and less than 2% of dimethylbicyclohexane compounds.

13. The process of claim 4, wherein the aromatic hydrocarbon is toluene and the hydroalkylation reaction product comprises less than 1 wt % of compounds containing in excess of 14 carbon atoms.

14. The process of claim 4, wherein the feed to step (a) further comprises benzene and/or at least one alkylbenzene different from toluene and xylene.

15. The process of claim 4, wherein the aromatic hydrocarbon is toluene and the dehydrogenation reaction product comprises less than 10 wt % of monomethyl-substituted biphenyl compounds.

16. The process of claim 4, wherein the aromatic hydrocarbon is toluene and the dehydrogenation reaction product comprises less than 5 wt % of fluorene and methylfluorenes combined.

17. The process of claim 4, wherein the dehydrogenation conditions in (b) include a temperature from about 200° C. to about 600° C. and a pressure from about 100 kPa to about 3550 kPa.

18. A process for producing biphenyl esters, the process comprising:
(a) contacting a feed comprising at least one aromatic hydrocarbon selected from the group consisting of toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes;
(b) dehydrogenating at least part of the hydroalkylation reaction product in the presence of a dehydrogenation catalyst under conditions effective to produce a dehydrogenation reaction product comprising a mixture of methyl-substituted biphenyl compounds, wherein the dehydrogenation catalyst comprises (i) an element or compound thereof from Group 10 of the Periodic Table of Elements and (ii) tin or a compound thereof;
(c) contacting at least part of the dehydrogenation reaction product with an oxygen source under conditions effective to convert at least part of the methyl-substituted biphenyl compounds to biphenyl carboxylic acids; and
(d) reacting the biphenyl carboxylic acids with one or more $C_4$ to $C_{14}$ alcohols under conditions effective to produce biphenyl esters.

19. The process of claim 18, wherein the hydroalkylation catalyst comprises an acidic component and a hydrogenation component.

20. The process of claim 19, wherein the acidic component of the hydroalkylation catalyst comprises a molecular sieve.

21. The process of claim 20, wherein the molecular sieve is selected from the group consisting of BEA, FAU and MTW structure type molecular sieves, molecular sieves of the MCM-22 family and mixtures thereof.

22. The process of claim 20, wherein the molecular sieve comprises a molecular sieve of the MCM-22 family.

23. The process of claim 18, wherein the hydroalkylation conditions in (a) include a temperature from about 100° C. to about 400° C. and a pressure from about 100 to about 7,000 kPa.

24. The process of claim 18, wherein the feed to step (a) further comprises benzene and/or at least one alkylbenzene different from toluene and xylene.

25. The process of claim 18, wherein the dehydrogenation conditions in (b) include a temperature from about 200° C. to about 600° C. and a pressure from about 100 kPa to about 3550 kPa.

26. The process of claim 4, wherein unreacted aromatic feed is removed from the hydroalkylation reaction product of step a) and recycled back to the hydroalkylation of step a).

27. The process of claim 4, wherein toluene and or xylene feed is removed from the hydroalkylation reaction product of step a) and recycled back to the hydroalkylation of step a).

28. The process of claim 4 wherein fully saturated single ring by-products in the hydroalkylation reaction product of step a) are dehydrogenated to produce recyclable feed that is recycled back to the hydroalkylation of step a).

29. The process of claim 4 wherein methylcyclohexane and dimethylcyclohexane in the hydroalkylation reaction product of step a) are dehydrogenated to produce recyclable feed that is recycled back to the hydroalkylation of step a).

30. The process of claim 4, wherein unreacted aromatic feed is removed from the hydroalkylation reaction product of step a) and recycled back to the hydroalkylation of step a), and wherein fully saturated single ring by-products in the hydroalkylation reaction product of step a) are dehydrogenated to produce recyclable feed that is recycled back to the hydroalkylation of step a).

31. The process of claim 4, wherein toluene and or xylene feed is removed from the hydroalkylation reaction product of step a) and recycled back to the hydroalkylation of step a), and wherein methylcyclohexane and dimethylcyclohexane in the hydroalkylation reaction product of step a) are dehydrogenated to produce recyclable feed that is recycled back to the hydroalkylation of step a).

32. The process of claim 18, wherein unreacted aromatic feed is removed from the hydroalkylation reaction product of step a) and recycled back to the hydroalkylation of step a), and wherein fully saturated single ring by-products in the hydroalkylation reaction product of step a) are dehydrogenated to produce recyclable feed that is recycled back to the hydroalkylation of step a).

33. The process of claim 18, wherein toluene and or xylene feed is removed from the hydroalkylation reaction product of step a) and recycled back to the hydroalkylation of step a), and wherein methylcyclohexane and dimethylcyclohexane in the hydroalkylation reaction product of step a) are dehydrogenated to produce recyclable feed that is recycled back to the hydroalkylation of step a).

34. A process for producing a methyl-substituted biphenyl compound, the process comprising:
(a) contacting at least one methyl-substituted cyclohexylbenzene compound of the formula:

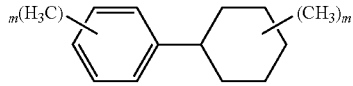

with a dehydrogenation catalyst under conditions effective to produce a dehydrogenation reaction product comprising at least one methyl-substituted biphenyl compound wherein each of m and n is independently an integer from 1 to 3 and wherein the dehydrogenation catalyst comprises (i) platinum and (ii) tin or a compound thereof; and the dehydrogenation reaction product comprises less than 10 wt % of monomethyl-substituted biphenyl compounds.

35. A process for producing methyl-substituted biphenyl compounds, the process comprising:
(a) contacting a feed comprising at least one aromatic hydrocarbon selected from the group consisting of toluene, xylene and mixtures thereof with hydrogen in the presence of a hydroalkylation catalyst under conditions effective to produce a hydroalkylation reaction product comprising (methylcyclohexyl)toluenes and/or (dimethylcyclohexyl)xylenes; and (b) dehydrogenating at least part of the hydroalkylation reaction product in the presence of a dehydrogenation catalyst under conditions effective to produce a dehydrogenation reaction product comprising a mixture of methyl-substituted biphenyl compounds, wherein the dehydrogenation catalyst comprises (i) platinum and (ii) tin or a compound thereof, wherein the hydroalkylation catalyst comprises an acidic component and a hydrogenation component, wherein the molecular sieve is selected from the group consisting of BEA, FAU, and MTW structure type molecular sieves, molecular sieves of the MCM-22 family and mixtures thereof.

36. The process of claim 35, wherein the molecular sieve comprises a molecular sieve of the MCM-22 family.

37. The process of claim 1, wherein the hydroalkylation reaction product comprises at least 60 wt % of the 3,3, 3,4, 4,3, and 4,4-isomers of (methylcyclohexyl)toluene based on the total weight of all the (methylcyclohexyl)toluene isomers, less than 30 wt % of methylcyclohexane, less than 2% of dimethylbicyclohexane compounds; and less than 1 wt % of compounds containing in excess of 14 carbon atoms.

38. The process of claim 1, wherein the hydroalkylation reaction product comprises at least 60 wt % of the 3,3, 3,4, 4,3, and 4,4-isomers of (methylcyclohexyl)toluene based on the total weight of all the (methylcyclohexyl)toluene isomers, less than 30 wt % of methylcyclohexane, less than 2% of dimethylbicyclohexane compounds; and less than 1 wt % of compounds containing in excess of 16 carbon atoms.

39. The process of claim 5, wherein the hydrogenation component of the hydroalkylation catalyst comprises platinum and tin.

* * * * *